(12) United States Patent
Phillips

(10) Patent No.: US 11,666,634 B2
(45) Date of Patent: Jun. 6, 2023

(54) METHODS AND COMPOSITIONS FOR MANAGEMENT OF GASTROINTESTINAL DISORDERS

(71) Applicant: THE BOARD OF REGENTS OF THE UNIVERSITY OF TEXAS SYSTEM, Austin, TX (US)

(72) Inventor: William T. Phillips, San Antonio, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 89 days.

(21) Appl. No.: 16/858,557

(22) Filed: Apr. 24, 2020

(65) Prior Publication Data
US 2020/0338167 A1    Oct. 29, 2020

Related U.S. Application Data

(60) Provisional application No. 62/838,200, filed on Apr. 24, 2019.

(51) Int. Cl.
| | | |
|---|---|---|
| *A61K 38/22* | (2006.01) | |
| *C07K 14/575* | (2006.01) | |
| *A61K 38/00* | (2006.01) | |
| *A61P 3/08* | (2006.01) | |
| *A61P 3/10* | (2006.01) | |
| *A61P 1/00* | (2006.01) | |
| *A61K 49/18* | (2006.01) | |
| *A61K 49/10* | (2006.01) | |

(52) U.S. Cl.
CPC .............. *A61K 38/22* (2013.01); *A61K 49/10* (2013.01); *A61K 49/1815* (2013.01); *A61P 1/00* (2018.01)

(58) Field of Classification Search
None
See application file for complete search history.

(56) References Cited

U.S. PATENT DOCUMENTS

| | | | | |
|---|---|---|---|---|
| 2010/0240587 A1* | 9/2010 | Schlein | .................. | A61K 38/22 514/6.8 |
| 2013/0281363 A1* | 10/2013 | Dahl | ....................... | A61P 29/00 514/6.9 |
| 2015/0051150 A1* | 2/2015 | Qui | ......................... | A61K 38/22 514/9.7 |

OTHER PUBLICATIONS

Donohoe et al., J. Nucl. Med. Techn. 37:196-200 (2009) (Year: 2009).*
McWhorter et al., Clin. Nucl. Med. 43:411-419 (2018) (Year: 2018).*
"Eliminate", Merriam-Webster, available online at https://www.merriam-webster.com/dictionary/eliminate, 7 pages (accessed on Apr. 6, 2022) (Year: 2022).*
Krishnasamy et al., Diabetes Ther. 9:S1-S42 (2018) (Year: 2018).*
Weinzimer et al., Diabetes Care 35:1994-1999 at p. 1994, col. 3, 2nd paragraph (2012) (Year: 2012).*
Newman, "What to know about indigestion or dyspepsia," Medical News Today, available online at www.medicalnewstoday.com/articles/163484, 14 pages (2023) (Year: 2023).*
NDDK, "Indigestion (Dyspepsia)", NDDK, available online at www.niddk.nih.gov/health-information/digestive-diseases/indigestion-dyspepsia#:~:text=You%20can%20help%20prevent%20indigestion%20by%20changing%20your%20diet.,%2C%20fatty%2C%20or%20greasy%20foods, 3 pages (accessed on Jan. 19, 2023) (Year: 2023).*

* cited by examiner

*Primary Examiner* — Thea D' Ambrosio
(74) *Attorney, Agent, or Firm* — Womble Bond Dickinson (US) LLP

(57) ABSTRACT

Described herein are methods of management of functional dyspepsia in a patient by administering an amylin analogue or a CCK composition to the patient. Methods of diagnosing such patient include a standard gastric-emptying assessment using a standardized solid meal along with measurements of blood glucose levels. Another method of diagnosing such patient includes a gastric-emptying scintigraphy assessment with labeled carbohydrates or other assessments to diagnose rapid carbohydrate gastric emptying.

6 Claims, 12 Drawing Sheets

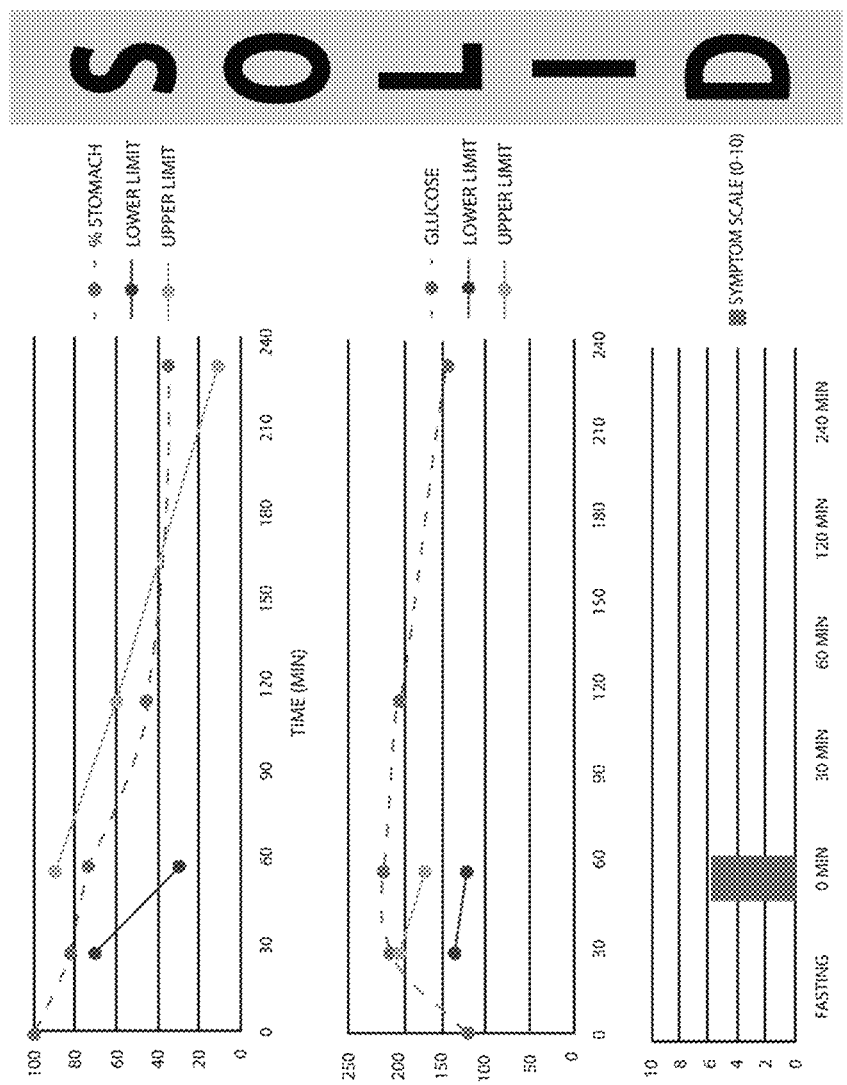

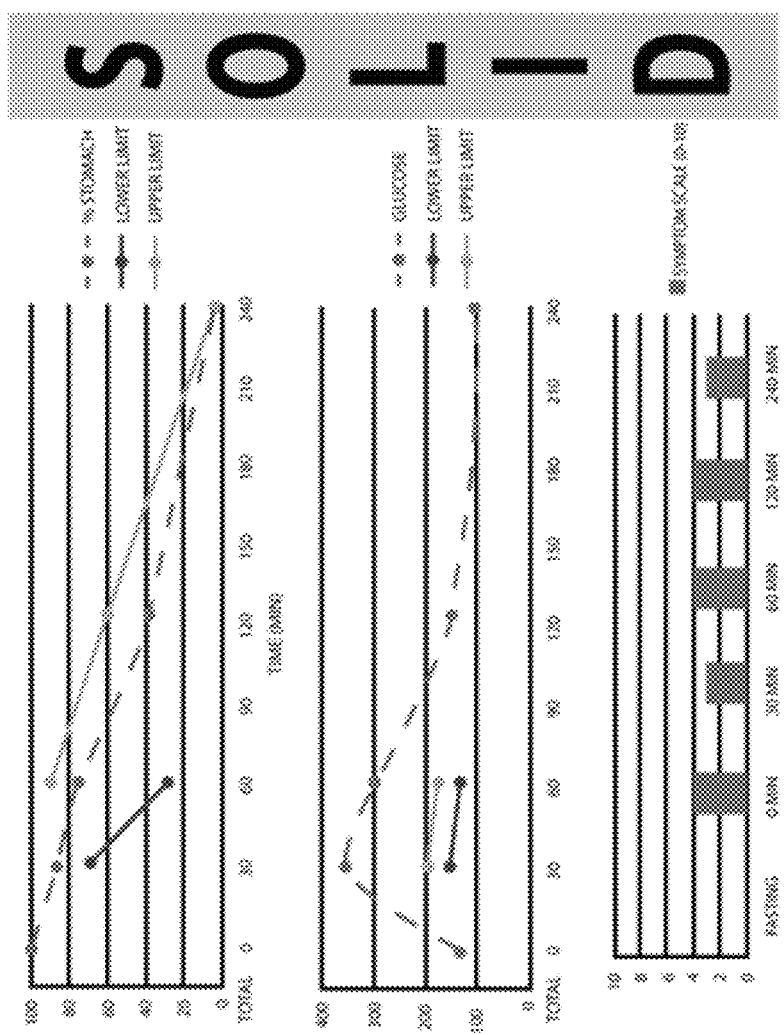

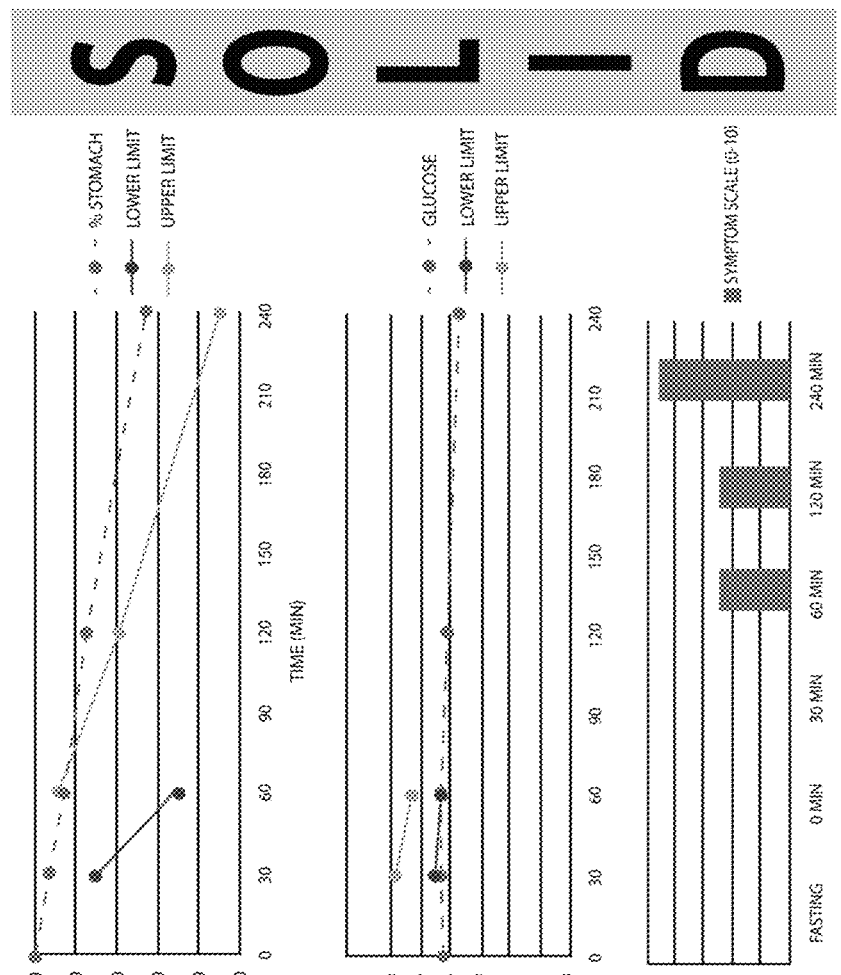

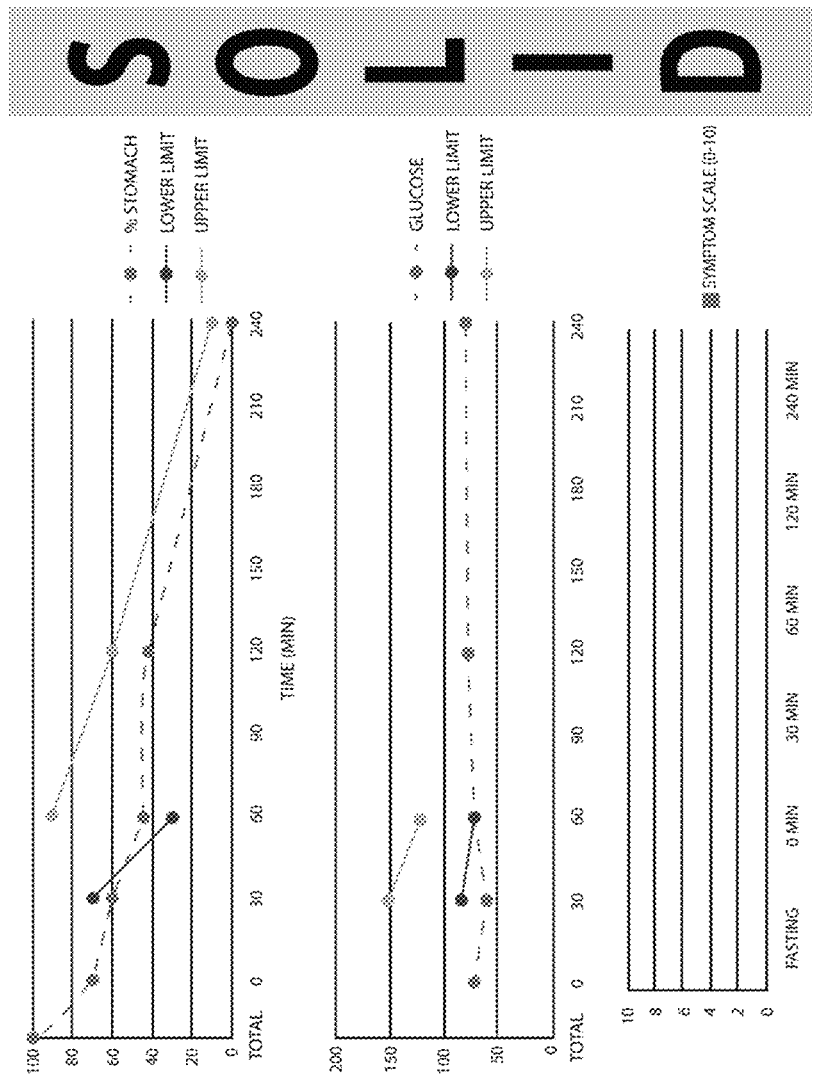

METHODS AND COMPOSITIONS FOR MANAGEMENT OF GASTROINTESTINAL DISORDERS

CROSS REFERENCE TO RELATED APPLICATIONS

This application claims priority to and the benefit of U.S. Provisional Application No. 62/838,200, filed Apr. 24, 2019, titled "Methods and Compositions for Management of Gastrointestinal Disorders," the entire contents of which are incorporated herein by reference.

TECHNICAL FIELD

This application relates to methods of treatment of functional dyspepsia.

BACKGROUND

Dyspepsia is a set of symptoms affecting the gastroduodenal region of the upper gastrointestinal tract. Symptoms include one or more upper gastrointestinal symptoms (such as reflux), epigastric pain, epigastric burning, postprandial fullness, and early satiety. Therefore, functional dyspepsia leads to a diminished quality of life. Functional dyspepsia is a very common condition with a yearly prevalence of about 10% of the adult population in the developed world. Functional dyspepsia is estimated to be a reason for 5% of all visits to primary care physicians and gastroenterology specialists. It has been estimated to be associated with 18 billion dollars in medical costs per year in the United States. A large-scale health and nutrition survey from France (which involved >35,000 people) identified that 15% of individuals had suspected functional dyspepsia, 28% had irritable bowel syndrome (IBS) and 6% had both. The population of patients who are affected by both IBS and functional dyspepsia has been reported to range between 10% and 27% in previous studies and to approach 30% in population samples; it could be even higher in specific populations. To date, treatments for functional dyspepsia have not been very effective and the mechanisms of functional dyspepsia have not been well understood.

SUMMARY

Provided here are compositions and methods addressing the shortcomings of the art and providing additional or alternative advantages. Described here are compositions and methods for management of functional dyspepsia. Embodiments include a pharmaceutical composition containing an amylin analogue or a pharmaceutically acceptable derivative thereof. Embodiments described herein include a pharmaceutical composition containing cholecystokinin or a cholecystokinin analogue or a pharmaceutically acceptable derivative thereof.

Embodiments disclosed here include methods of treatment of functional dyspepsia. One such method includes the steps of classifying the subject as having normal, rapid, or delayed gastric emptying based on a gastric-emptying assessment; classifying the subject as having elevated, normal, or diminished glycemic excursion based on one or more blood glucose levels of the subject as measured during the gastric-emptying assessment; and administering an amylin analogue to the subject upon being classified as having delayed gastric emptying and elevated glycemic excursion. In an embodiment, the amylin analogue is pramlintide. The pramlintide can be administered via a parenteral route. In an embodiment, the gastric-emptying assessment is a standard gastric-emptying scintigraphy assessment using a standardized solid meal.

Another method of treatment of functional dyspepsia includes the steps of classifying the subject as having normal, rapid, or delayed gastric emptying based on a gastric-emptying assessment; classifying the subject as having elevated, normal, or diminished glycemic excursion based one or more measurements of blood glucose levels of the subject during the gastric-emptying assessment; and administering a cholecystokinin composition to the subject upon being classified as having delayed gastric emptying and elevated glycemic excursion. In an embodiment, the cholecystokinin composition contains cholecystokinin or a cholecystokinin analogue. In an embodiment, the gastric-emptying assessment is a standard gastric-emptying scintigraphy assessment using a standardized solid meal.

In an embodiment, the subject is classified as having rapid gastric emptying if the subject has emptied one or more of a greater than 30% of a standardized solid meal at 30 minutes or a greater than 70% of the standardized solid meal at 1 hour. In an embodiment, the subject is classified as having delayed gastric emptying if the subject has emptied either less than 90% of the meal at 4 hours, or less than 10% of the meal at 1-2 hours. In an embodiment, the subject is classified as having an elevated glycemic excursion if the blood glucose level above baseline was greater than 75 milligrams per deciliter (mg/dL) at 30 minutes or greater than 85 mg/dL at 1 hour. In an embodiment, the subject is classified as having normal glycemic excursion if the blood glucose level above baseline was greater than 30 mg/dL but less than 75 mg/dL at 30 minutes or greater than 30 mg/dL but less than 85 mg/dL at 1 hour. In an embodiment, the subject is classified as having diminished glycemic excursion if the blood glucose level above baseline was less than 30 mg/dL at 30 minutes. In an embodiment, the subject is a non-diabetic individual.

Numerous other aspects, features and benefits of the present disclosure may be made apparent from the following detailed description taken together with the figures. The pharmaceutical compositions can include compositions described herein along with other components, or ingredients depending on desired prevention and treatment goals. It should be further understood that both the foregoing general description and the following detailed description are exemplary and explanatory and are intended to provide further explanation of the embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments will be readily understood by the following detailed description in conjunction with the accompanying drawings. Embodiments are illustrated by way of example and not by way of limitation in the accompanying drawings.

FIGS. 1A-1C are graphical representations of normal solid gastric emptying (FIG. 1A), a normal postprandial glucose excursion of normal nondiabetic patient (FIG. 1B), and a symptom scale (FIG. 1C) of a normal nondiabetic patient.

FIGS. 4A-4C are graphical representations of normal solid gastric emptying (FIG. 4A), elevated postprandial glycemic excursion (FIG. 4B) and a symptom scale (FIG. 4C) of a patient.

FIGS. 5A-5C are graphical representations of delayed solid gastric emptying (FIG. 5A), diminished postprandial glycemic excursion (FIG. 5B) and a symptom scale (FIG. 5C) of a diabetic patient.

FIGS. 7A-7C are graphical representations of rapid initial solid gastric emptying (FIG. 7A), diminished postprandial glycemic excursion (FIG. 7B) and a symptom scale (FIG. 7C) of a patient.

DETAILED DESCRIPTION

Figures 2A, 2B, 2C:
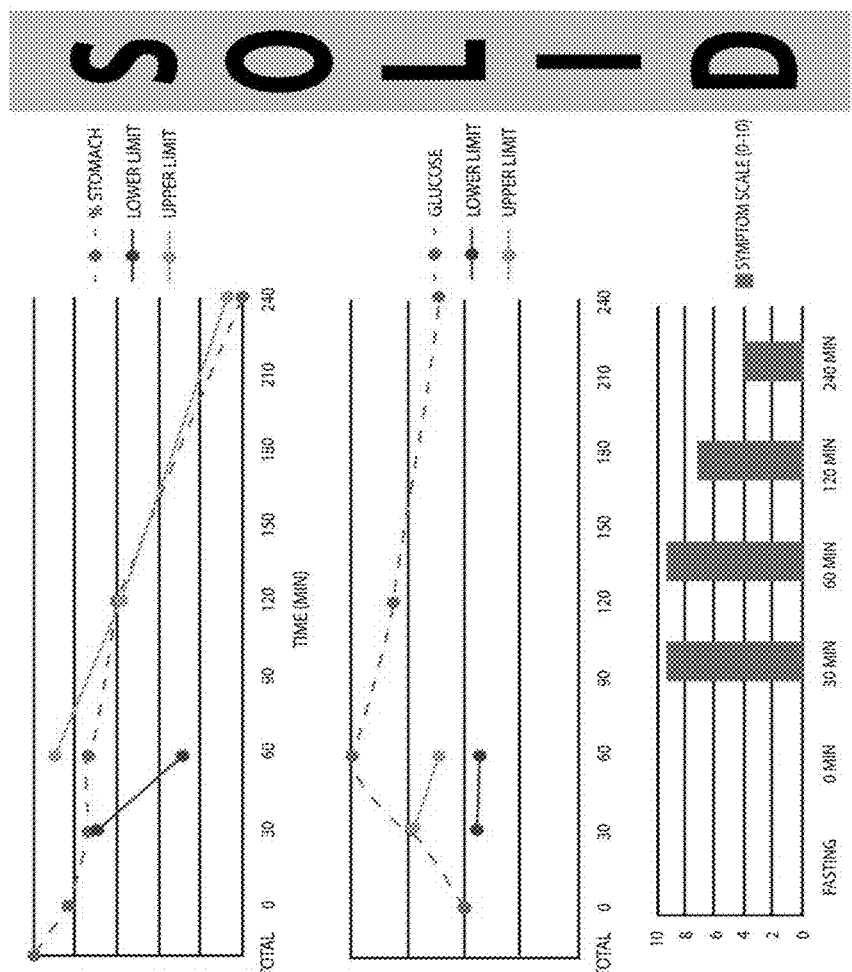
FIGS. 2A-2C are graphical representations of delayed solid gastric emptying (FIG. 1A), an elevated glycemic excursion of 97 mg/dL of a patient (FIG. 2A), and a symptom scale (FIG. 2C) of a patient.

Reference will now be made to the exemplary embodiments illustrated in the drawings, and specific language will be used here to describe the same. It will nevertheless be understood that no limitation of the scope of the disclosure is thereby intended. Alterations and further modifications of the inventive features illustrated here, and additional applications of the principles of the embodiments as illustrated here, which would occur to one skilled in the relevant art and having possession of this disclosure, are to be considered within the scope of the disclosure.

Disclosed here are novel therapeutic approaches that are effective for many cases of functional dyspepsia. Methods of management of functional dyspepsia include administering an amylin analogue or a cholecystokinin (CCK) analogue to a patient. Methods of diagnosing such a patient include a standard gastric-emptying scintigraphy assessment using a standardized solid meal along with one or more measurements of blood glucose levels of the subject. Another method of diagnosing such patient includes a gastric-emptying scintigraphy assessment with labeled carbohydrates or other assessments to diagnose rapid carbohydrate gastric emptying, such as a liquid glucose gastric-emptying scintigraphy assessment.

An embodiment of a method of treatment of functional dyspepsia includes the steps of classifying the subject as having normal, rapid, or delayed gastric emptying based on a gastric-emptying scintigraphy assessment using a standardized solid meal; classifying the subject as having elevated, normal, or diminished glycemic excursion based on one or more measurements of blood glucose levels of the subject during the gastric-emptying scintigraphy assessment; and administering an amylin analogue to the subject upon being classified as having delayed gastric emptying and elevated glycemic excursion. The amylin analogue is pramlintide. The pramlintide is administered via a parenteral route. In certain embodiments, the subject is non-diabetic.

A significant number of patients were found to have unsuspected rapid gastric emptying of the carbohydrate portion of meals even though the solid labeled portion of the meal emptied either normally or abnormally slowly. In this study, 86 out of 172 patients with normal or delayed solid gastric emptying also had an abnormally elevated postprandial glycemic excursion consistent with unsuspected rapid carbohydrate gastric emptying. Previously, these 86 patients would have been diagnosed with normal gastric emptying or delayed gastric emptying of the solid egg meal component. Based on novel approaches disclosed here, these patients were diagnosed as having rapid gastric emptying of the carbohydrate containing components of the meal. This rapid gastric emptying which occurs soon after meal consumption correlates with the time period that is characteristic of functional dyspepsia. A significant number of these patients with elevated postprandial glucose levels have postprandial pain in the first hour after meal consumption. Therefore, a method of treatment of a patient with functional dyspepsia includes the administration of a pharmaceutical composition that contains a hormonal agent to slow gastric emptying.

Agents that slow gastric emptying are used for the treatment of diabetes. But these agents are not prescribed for the treatment of functional dyspepsia, particularly in non-diabetic patients. Disclosed here are the methods of use of amylin analogues in the treatment of non-diabetic patients with functional dyspepsia. Another class of drugs that could be used to delay postprandial gastric emptying are the CCK analogues.

In the art, patients with post-prandial distress syndrome are prescribed one or more prokinetic drugs, such as domperidone, metoclopramide, alizapride, clebopride, itopride, or cinitapride. These patients are also prescribed fundus-relaxing drugs, such as acotiamide, busiprone, tandospirone, or other 5-hydroxytryptamine-1A receptor agonists. Certain patients are also prescribed centrally active neuromodulators, such as mirtazapine. Patients with epigastric pain syndrome are prescribed acid-suppressive drugs, such as omeprazole, lansoprazole, pantoprazole, esomeprazole, rabeprazole, ranitidine, or others. These patients are then prescribed tricyclinc antidepressants, such as amitriptyline, nortriptyline, desipramine, or other drugs. Although there are so many different therapies prescribed, none work that well indicating an inadequate understanding of the physiology of functional dyspepsia. A substantial portion of patients with functional dyspepsia have abnormalities of gastric emptying and the current recommendation is to prescribe prokinetic agents, i.e. agents that accelerate the rate of gastric emptying. Unfortunately, these prokinetic therapies would only be effective in patients that have truly delayed gastric emptying. These therapies would not benefit patients with postprandial pain in the first hour, who have elevated glycemic excursions consistent with rapid carbohydrate emptying.

The mechanisms of functional dyspepsia are related to the lack of monitoring of the carbohydrate portion of the meals used to study gastric emptying rates. In the study disclosed here, 26 out of 54 patients have delayed gastric emptying of the solid meal component, but also have an elevated glycemic excursion consistent with rapid gastric emptying of the carbohydrate meal components. The delayed gastric emptying in these patients is due to "feedback gastroparesis" in which the elevated postprandial glucose levels, secondary to rapid carbohydrate emptying feedback to the stomach through the vagus nerve, cause a delayed gastric emptying of the remaining solid meal component. In these patients with rapid initial carbohydrate emptying, a prokinetic agent will not help their symptoms and these agents do not seem to be very effective for treating the condition.

Embodiments of the method of management of functional dyspepsia include the use of a naturally occurring hormonal agent that slows gastric emptying in non-diabetic patients. Observations from the study indicate that 30% of non-diabetic patients referred for gastric emptying studies due to gastrointestinal symptoms have elevated postprandial glycemic excursions and that elevated postprandial glycemic excursions are due to rapid gastric emptying of the carbohydrate portion of the meal. This rapid gastric emptying is frequently associated with significant pain during the first hour after a meal. Embodiments of the disclosure include agents that slow down this rapid gastric emptying and alleviate the postprandial symptoms. These agents will also lower the abnormally elevated postprandial rise in glucose and blunt any feedback from elevated glucose levels, and therefore, smooth out these patients overall gastric emptying rate of carbohydrates, proteins, and fats. In these patients with functional dyspepsia, rapid gastric emptying and elevated postprandial glucose levels increase risk of future development of diabetes. This treatment will delay gastric emptying and lower postprandial glucose levels and will have a preventive effect in these patients on their future development of diabetes.

Diabetic patients have been treated with the glucagon-like peptide-1 (GLP-1) analogues, which delay gastric emptying, but also reduce glucose levels through the stimulation of insulin. Embodiments of compositions disclosed here are compositions that delay or slow gastric emptying but do not stimulate insulin. Embodiments include pharmaceutical compositions containing amylin analogues or cholecystokinin (CCK) analogues or combinations or pharmaceutically acceptable derivatives thereof, which slow gastric emptying hormonally but do not have any effects on insulin. Thus, these compositions can be safely used in non-diabetic patients.

Embodiments include pharmaceutical compositions containing an amylin analogue, such as pramlintide, or a pharmaceutically acceptable derivative. Although, pramlintide was originally introduced for diabetes treatment, it has been superseded by agents that not only delayed gastric emptying but also stimulated insulin secretion. Pramlintide is one of the agents disclosed here for treating functional dyspepsia in non-diabetic patients, because it does not stimulate insulin. Anti-cholinergic agents can be used to delay gastric emptying, but these agents are associated with significant side effects such as dry mouth, dry eyes, constipation and urinary retention. Natural endogenous hormonal agents, such as pramlintide, do not have this anti-cholinergic side effects and are more effective at delayed gastric emptying and therefore treating functional dyspepsia.

As used here, the following terms may have the following definitions. A "pharmaceutical composition" refers to one or more of the agents that slow gastric emptying but do not have any effects on insulin as described herein, or a pharmaceutically acceptable derivative thereof as an active ingredient. The purpose of a pharmaceutical composition is to facilitate administration of an agent, such as an amylin analogue, in a therapeutically effective amount to a subject. In another embodiment, the pharmaceutical composition includes a CCK analogue.

In another aspect, a pharmaceutical composition includes an agent described herein, or a pharmaceutically acceptable salt thereof, and a pharmaceutically acceptable carrier or excipient. In some embodiments, the pharmaceutical composition includes two or more pharmaceutically acceptable carriers and/or excipients. The term "pharmaceutically acceptable derivative" as used herein refers to and includes any pharmaceutically acceptable salt, pro-drug, metabolite, ester, ether, hydrate, polymorph, solvate, complex, and adduct of a composition described herein which, upon administration to a subject, is capable of providing (directly or indirectly) the active ingredient. As used herein, the term "pharmaceutically acceptable salt" refers to those salts which retain the biological effectiveness and properties of the parent composition. And unless otherwise indicated, a pharmaceutically acceptable salt includes salts of acidic or basic groups which may be present in the agents disclosed herein. Certain embodiments relate to pharmaceutically acceptable salts of agents that slow gastric emptying hormonally but do not have any effects on insulin, their derivatives, their analogues, their tautomeric forms, their stereoisomers, their polymorphs and pharmaceutically acceptable compositions containing them. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, beta-hydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydro genphosphate, dihydrogenphosphate, metaphosphate, pyrophosphate, propionate, phenylpropionate, salicylate, succinate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

Embodiments include one or more agents that slow gastric emptying but do not have any effects on insulin, or a pharmaceutically acceptable salt thereof, and a pharmaceutically acceptable carrier or excipient. Pharmaceutically acceptable ingredients, such as excipients, diluents, fillers, binders, and carriers can be inert or actively contribute to the delivery and distribution of the compositions. The formulations used in embodiments herein include excipients, such as microcrystalline cellulose, lactose monohydrate, hydroxypropyl cellulose, croscarmellose sodium and magnesium stearate, preferably at least about 50 wt %, such as in the range from about 50% to about 95 wt %, including the range from about 50-90 wt %, and more preferably in the range from about 55-85 wt %, such as in the range from about 60% to about 85 wt %, or in the range from about 65 wt % to about 80 wt %, including about 60 wt %, about 65 wt %, about 70 wt %, about 75 wt %, or about 80 wt %.

As used herein, unless otherwise noted, the terms "treating", "treatment" and the like, shall include the management and care of a subject or patient (preferably mammal, more preferably human) for the purpose of combating a disease, condition, or disorder and includes the administration of an agent as disclosed here to prevent the onset of the symptoms or complications, alleviate the symptoms or complications, or eliminate the disease, condition, or disorder. The compositions herein are formulated in accordance to the mode of potential administration. The pharmaceutical compositions for parenteral administration may contain one or more of buffers, solvents, antioxidants, preservatives, suspending agents, thickening agents, and solutes, which render the composition suitable for entering the bloodstream of the patient. These pharmaceutical compositions can be packaged in unit-dose or multi-dose containers as fluid compositions. In other embodiments, these pharmaceutical compositions can be packaged as freeze-dried/lyophilized compositions requiring only the addition of the sterile fluid before administration to a patient. In certain embodiments, these pharmaceutical compositions are formulated for intramuscular administration. Compositions for administration herein may form solutions, suspensions, tablets, pills, capsules, sustained release formulations or powders.

Optimal dosages to be administered may be readily determined by those skilled in the art, and will vary with the particular composition used, the mode of administration, the strength of the preparation, the mode of administration, the number of consecutive administrations within a limited period of time (e.g. up to 60 minutes) and the advancement of the disease condition. In addition, factors associated with the particular patient being treated, including patient age, weight, diet and time of administration, will result in the need to adjust dosages. The term "subject" as used herein, refers to an animal, preferably a mammal, most preferably a human, who has been the object of treatment, observation, or experiment. Preferably, the subject has experienced or exhibited at least one symptom of the disease or disorder to be treated or prevented.

An embodiment of a method of treatment of functional dyspepsia includes the steps of classifying the subject as having normal, rapid, or delayed gastric emptying based on a gastric-emptying assessment; classifying the subject as having elevated, normal, or diminished glycemic excursion based on one or more measurements of blood glucose levels of the subject during the gastric-emptying assessment; and administering an agent to the subject upon being classified as having delayed gastric emptying and elevated glycemic excursion. Gastric-emptying can be assessed by any test that evaluates the movement of ingested materials from the stomach, such as gastric emptying scintigraphy (GES), magnetic resonance imaging (MM), and ultrasonography (US), breath testing, and wireless pH capsules. Patients can be classified as having normal, rapid, or delayed gastric emptying based on criteria specified in the gastric-emptying assessment.

An embodiment of a method of treatment of functional dyspepsia includes the steps of classifying the subject as having normal, rapid, or delayed gastric emptying based on a gastric-emptying scintigraphy assessment using a standardized solid meal; classifying the subject as having elevated, normal, or diminished glycemic excursion based on one or more measurements of blood glucose levels of the subject during the gastric-emptying scintigraphy assessment; and administering an agent to the subject upon being classified as having delayed gastric emptying and elevated glycemic excursion. One method for assessment of gastric-emptying abnormalities is the standardized solid radiolabeled egg-white gastric-emptying protocol. In the standardized gastric-emptying meal, egg white is radiolabeled with $^{99m}$Tc-sulfur colloid (SC) and combined with 2 pieces of toast and strawberry jam. However, the majority of the meal's kilocalorie content is contained in the high-carbohydrate toast and jam (76% of the total kilocalorie meal content); these high-carbohydrate components are not radiolabeled. Hence, the meal's carbohydrate impact on gastric-emptying rate is not assessed, which may be significant, because prior studies have reported that different meal components can frequently empty at different rates. In a comparative study, a radiolabeled high-carbohydrate component of a mixed nutrient meal emptied 30 minutes more rapidly than the radiolabeled hamburger/protein component.

Differences in the gastric-emptying rates of various meal components are understandable considering that carbohydrates have very different digestive mechanisms compared with protein. For instance, while in the mouth, bread particles are well degraded hydrolysis, which may accelerate their gastric emptying. Carbohydrates, proteins, and fats stimulate different incretin hormones that play important roles to regulate gastric emptying, raising the possibility that patients may have gastric-emptying variations related to isolated macronutrients. For example, carbohydrates stimulate GLP-1 secretion in the small intestine, a major moderator of the gastric emptying of carbohydrates, whereas protein gastric emptying is moderated via intestinal secretion of PYY. The most commonly used meals in clinical gastric-emptying scintigraphy (GES) radiolabel only the protein component of a mixed meal, and thus, carbohydrate gastric-emptying differences may remain undetected. The unlabeled carbohydrate component of the standardized egg meal often empties more rapidly than the radiolabeled protein component, and this rapid carbohydrate emptying may lead to variable gastric-emptying effects not detected with current imaging methods. Abnormally rapid carbohydrate emptying may be an unidentified cause of postprandial gastrointestinal symptoms.

In an embodiment, patients were classified as having normal, rapid, or delayed gastric emptying based on criteria specified in the standardized $^{99m}$Tc—SC solid meal gastric-emptying protocol. According to this convention, "delayed" gastric emptying is defined as having more than 10% of the meal remaining in the stomach at 4 hours. Based on criteria for the standardized solid meal, patients were classified as having rapid solid gastric emptying if they emptied greater than 30% of the meal at 30 minutes and/or greater than 70% of the meal at 1 hour, delayed gastric emptying at 4 hours if they emptied less than 90% of the meal, and delayed emptying at 1 and 2 hours only if they emptied less than 10% of the meal. Patients were further subcategorized according to postprandial glycemic excursions above baseline at 30 minutes or 1 hour. Glycemic excursions can be measured by any suitable blood glucose monitoring method. These blood glucose monitoring methods can include intermittent glucose monitoring or continuous glucose monitoring. Postprandial glucose excursion was considered to be "elevated" if the glycemic excursion above baseline was greater than 75 mg/dL at 30 minutes or greater than 85 mg/dL at 1 hour. A postprandial glycemic excursion was considered "normal" if the elevation above the fasting baseline was greater than 30 mg/dL but less than 75 mg/dL at 30 minutes or greater than 30 mg/dL but less than 85 mg/dL at 1 hour. Patients were classified as having a "diminished" glycemic excursion if the serum glucose elevation at 30 minutes was less than 30 mg/dL above baseline glucose levels.

In an embodiment, intermittent serial blood glucose measurements during GES was utilized as a surrogate marker for gastric-emptying patterns of the unlabeled carbohydrate components in the standardized radiolabeled egg-white meal. The rate of carbohydrate gastric emptying is highly correlated with 30-minute and 1-hour postprandial glucose excursions above baseline. The postprandial glucose excursions were significantly correlated with gastric emptying at 30 minutes (R=−0.58, P<0.05). Diabetic subjects had 1-hour blood glucose excursions that significantly correlated with gastric half-emptying times (R=−0.65, P=0.0001). All normal and diabetic patients with postprandial serum glucose excursions of greater than 75 mg/dL above their fasting baseline levels at 30 minutes were found to have abnormally rapid gastric emptying of a liquid carbohydrate meal composed of a flavored glucose solution having an osmolality (0.62 molar) similar to commercial juice and soda beverages. On the other hand, all subjects with normal gastric-emptying rates had glucose excursions of less than 60 mg/dL at 30 minutes and 1 hour.

Patients were classified as normal, rapid, or delayed gastric emptying from the standardized solid egg meal GES criteria. Further subcategorization was made based on postprandial glycemic excursions above baseline at 30/60 minutes and was delineated as elevated (>75 mg/>85 mg/dL), normal, or diminished (<30 mg/dL) glucose excursion. Simultaneous blood glucose monitoring with standardized GES protocols may provide a marker for contradictory findings of rapid gastric emptying of the unlabeled carbohydrate component in the standardized meal and may contribute to unexplained postprandial gastrointestinal symptoms. The additional insights provided by fingerstick glucose monitoring are inexpensive, easy to perform and may provide for new approaches to management of patient's gastrointestinal symptoms.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein. To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. The following non-limiting examples are provided in order to further illustrate the present disclosure.

EXAMPLES

The following Examples are set forth to aid in the understanding of the disclosure, and are not intended and should not be construed to limit in any way the invention set forth in the claims which follow thereafter.

Example 1

The retrospective evaluation of 197 consecutive patients was conducted and these patients had been subject to a solid standardized radiolabeled egg-white, toast, and jam GES evaluation over a 2-year period and also had simultaneous fingerstick blood glucose measurements at each time point of acquisition of the gastric scintigraphy images (baseline, 0.5, 1, 2, and 4 hours) using methodology described in a consensus statement for the standardized egg-white meal by the nuclear medicine and gastroenterology societies. These 197 consecutive patients were referred for GES from Jan. 1, 2015, to Mar. 31, 2017, for evaluation of postprandial abdominal pain or other gastrointestinal symptoms such as vomiting and bloating. For comparative purposes, consecutive patients were excluded from this retrospective review if they did not complete consumption of 100% of the standardized solid radiolabeled egg-white meal. All patients were given the standardized solid $^{99m}$Tc—SC radiolabeled egg-white meal containing 120 g of egg white (61 kcal), 2 slices of white bread (120 kcal), and 30 g of strawberry jam (74 kcal, total kilocalorie content of 255 kcal) radiolabeled with 1 mCi $^{99m}$Tc—SC with imaging performed according to the 2007 American College of Radiology/Society of Nuclear Medicine/Society for Pediatric Radiology Practice Guideline for the Performance of Gastrointestinal Scintigraphy based on international control values. Static 1-minute images were obtained in the anterior and posterior positions with regions of interest drawn around the stomach in the anterior and posterior positions, and geometric mean calculation of the percent retained in the stomach was measured.

Importantly, on the first set of anterior and posterior images acquired immediately after meal consumption, a region of interest was drawn around both the stomach and the whole abdomen on both the anterior and posterior images to determine the amount of meal emptied during the time of meal consumption. In addition, all patients had blood glucose measurements by finger-stick glucometer prior to meal consumption and at 0.5, 1, 2, and 4 hours post-meal consumption. Blood glucose measurements were made immediately prior to acquisition of 1-minute planar anterior and posterior gastric scintigraphy. In addition, patient-specific symptoms were recorded before and during all imaging time points and ranked on a scale of 1 to 10, with 1 being mild nausea or discomfort and 10 being the most severe nausea or discomfort. During the last half of the period for these GES studies, patients who were noted to have either normal or delayed gastric emptying while also having an elevated glycemic excursion were recommended to return for an additional liquid glucose GES study.

Seven of these patients had type 2 diabetes and two had no diabetes. During this time, 9 patients with normal or delayed gastric emptying also in addition to abnormally elevated glycemic excursions were referred back for a follow-up liquid glucose carbohydrate gastric-emptying study. The liquid glucose meal was composed of 50 g of glucose in 450 mL of water (200 kcal, 0.62 molar) containing 1 mCi $^{99m}$Tc—SC. Normal gastric-emptying rates for this liquid glucose meal protocol were previously described in prior studies published by the inventor's research group. Comparisons of the standardized egg-white GES to the liquid glucose GES results in each of these 9 patients were analyzed using normal gastric-emptying parameters for each meal. Means and SDs of GER, along with normal parameters, were plotted for each study. Postprandial glycemic and the liquid glucose meal and statistically analyzed using paired t testing.

Figure 8:
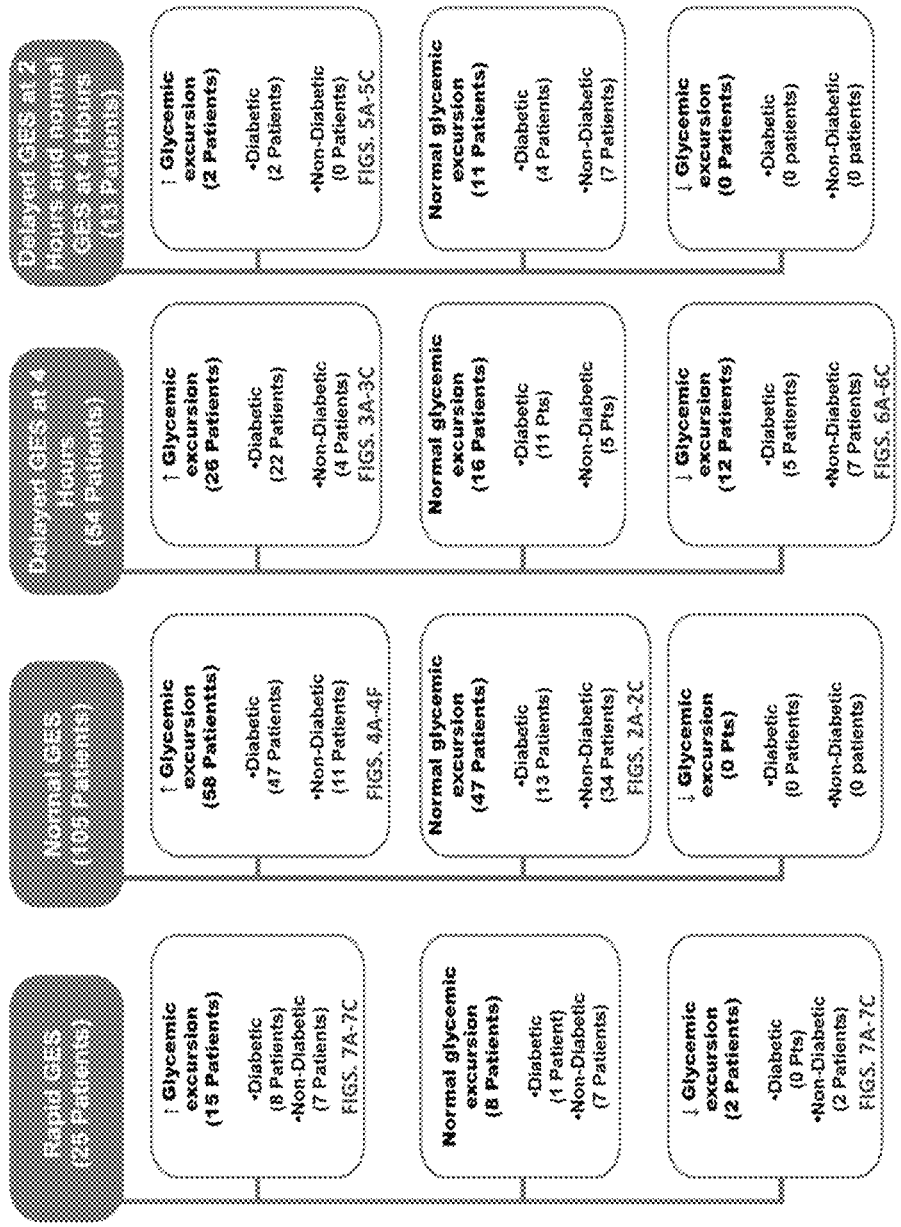
FIG. 8 is an illustration showing the classification of 197 patients with rapid, normal, and delayed solid emptying, which are further classified into those with elevated, normal, or diminished postprandial glycemic excursions during the first postprandial hour in patients with and without diabetes. Examples in typical patients in some of the categories above are shown in FIGS. 1A-1C, 2A-2C, 3A-3C, 4A-4F, 5A-5C, 6A-6C, and 7A-7C.

The results are shown in FIG. 8. Of the 197 consecutive patients referred for gastrointestinal symptoms, 112 had diabetes and 75 had no diabetes. One hundred five patients had normal solid gastric emptying, 54 patients had delayed solid emptying at 4 hours, 13 patients had initially delayed solid emptying 1 or 2 hours with normal solid emptying at 4 hours, and 25 patients had rapid solid emptying based on the classification for solid gastric emptying of standardized solid egg-white meal (Table 1).

TABLE 1

Solid Gastric-Emptying Results in 197 Consecutive Patients Classified by Standardized Low-Fat Egg-White Meal Criteria

| | |
|---|---|
| Rapid solid emptying >30% emptied at 0.5 h and >70% emptied at 1 h | 25 |
| Normal solid emptying <30% emptied at 0.5 h and <70% emptied at 1 h and >90% emptied at 4 h | 105 |
| Delayed emptying at 4 h <90% emptied at 4 h | 54 |
| Delayed emptying at 1 or 2 h but normal emptying at 4 h <10% emptied at 1 h and/or <40% emptied at 2 h, but >90% at 4 h | 13 |

One hundred one of the 197 patients had elevated glycemic excursions. Of these patients, 70.5% had diabetes and 29.3% had no diabetes (Table 2).

TABLE 2

Classification of Patients With Elevated Glycemic Excursions for Diabetes and Solid Emptying Rate in 101 of 197 Consecutive Patients

| Solid Emptying | Patients With Diabetes | Patients With No Diabetes |
|---|---|---|
| Rapid solid emptying (15/25) | 8 | 7 |
| Normal solid emptying (58/105) | 47 | 11 |
| Delayed solid emptying 4 h (26/54) | 22 | 4 |
| Delayed solid emptying at 1 and 2 h (2/13) | 2 | 0 |
| % of patients | 70.5 | 29.5 |

There were 105 patients with normal gastric emptying, with 58 of these patients having elevated postprandial glycemic excursions, 47 having normal glycemic excursions, and none having minimal glycemic excursions. Of the 54 patients with delayed gastric emptying (at 4 hours), 26 had elevated glycemic excursions, 16 had normal glycemic excursions, and 12 patients had diminished glycemic excursions (FIG. 8). There were 13 patients with initially delayed gastric emptying at 1 or 2 hours but normal gastric emptying at 4 hours, with 2 patients having elevated glycemic excursions, 11 having normal glycemic excursions, and none having diminished glycemic excursions. A majority of the 25 patients (15 patients) with rapid solid gastric emptying had abnormally elevated glycemic excursions, whereas 8 had normal glycemic excursions, and 2 patients had diminished glycemic excursions. Forty-seven of the 197 patients had normal solid gastric emptying and normal glycemic excursions. A typical patient with normal gastric-emptying study and normal postprandial glycemic excursion is shown in FIGS. 1A-1C. FIGS. 1A-1C are graphical representations of normal solid gastric emptying (FIG. 1A), a normal postprandial glucose excursion of normal nondiabetic patient (FIG. 1B), and a symptom scale (FIG. 1C) of a normal nondiabetic patient.

Fifty-four patients had delayed GES results. Nearly 50% (26/54) of these patients with delayed GES also had elevated postprandial glucose excursions. An example of a patient with this pattern is shown in FIGS. 2A-2C. FIGS. 2A-2C are graphical representations of delayed solid gastric emptying (FIG. 1A), an elevated glycemic excursion of 97 mg/dL of a patient (FIG. 2A), and a symptom scale (FIG. 2C) of a patient. The prolonged elevation of glucose levels may be causing a glucose "feedback gastroparesis" with 33% of the ingested meal remaining in the stomach at 4 hours. During this study, the patient had significant pain (6/10) immediately after eating the complete meal. This patient's postprandial glucose excursions above baseline of 78 mg/dL at 30 minutes and 97 mg/dL at 1 hour are consistent with rapid carbohydrate emptying.

Figures 3A, 3B, 3C:
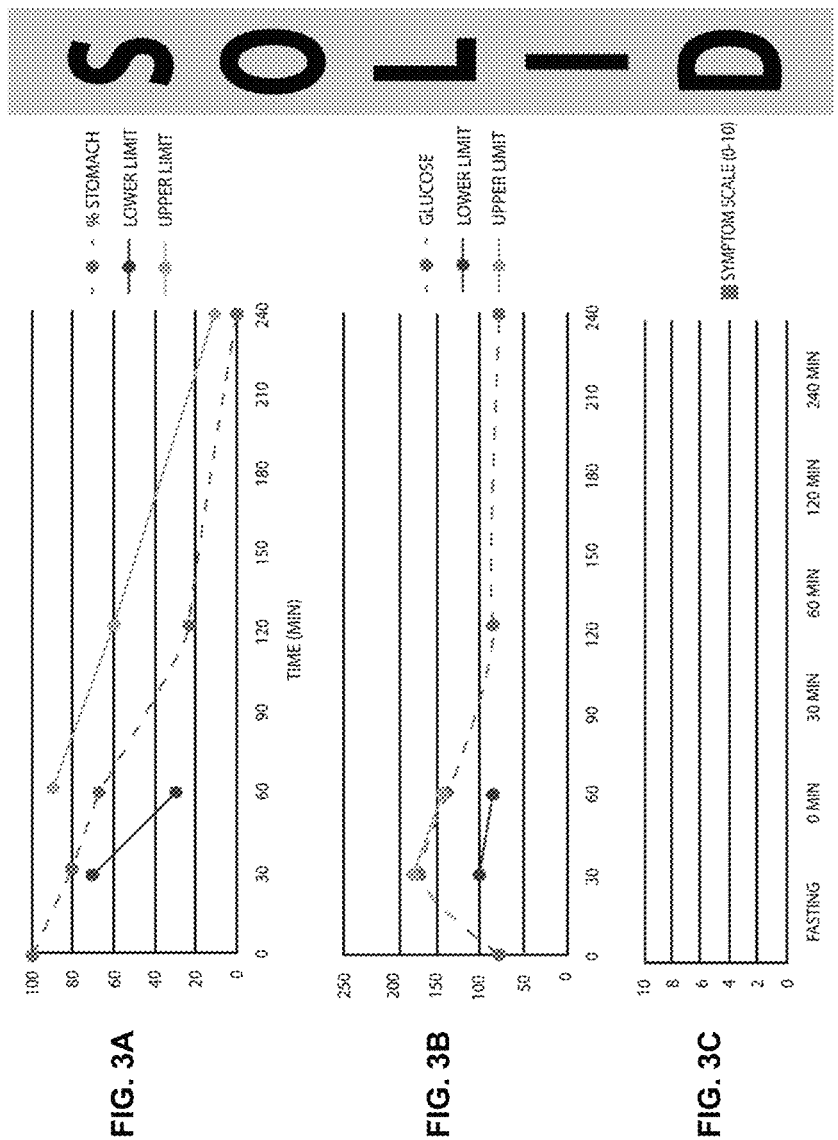
FIGS. 3A-3C are graphical representations of delayed solid gastric emptying at 2 hours, which normalized at 4 hours (FIG. 3A), elevated postprandial glycemic excursion (FIG. 3B) and a symptom scale (FIG. 3C) of a patient.

Thirteen of the 197 patients had initially delayed gastric emptying (at 1 and/or 2 hours but normal gastric emptying at 4 hours), with a typical patient shown in FIGS. 3A-3C. FIGS. 3A-3C are graphical representations of delayed solid gastric emptying at 2 hours, which normalized at 4 hours (FIG. 3A), elevated postprandial glycemic excursion (FIG. 3B) and a symptom scale (FIG. 3C) of a patient. Note the very significantly elevated postprandial glycemic excursion above baseline at 30 minutes (86 mg/dL) and at 1 hour (193 mg/dL) associated with pain score of 9 out of 10 at 30 minutes and 1 hour. Also, note the pause in gastric emptying from 30 minutes to 1 hour, which normalized by 4 hours when blood glucose levels approached baseline levels.

Figures 4D, 4E, 4F:
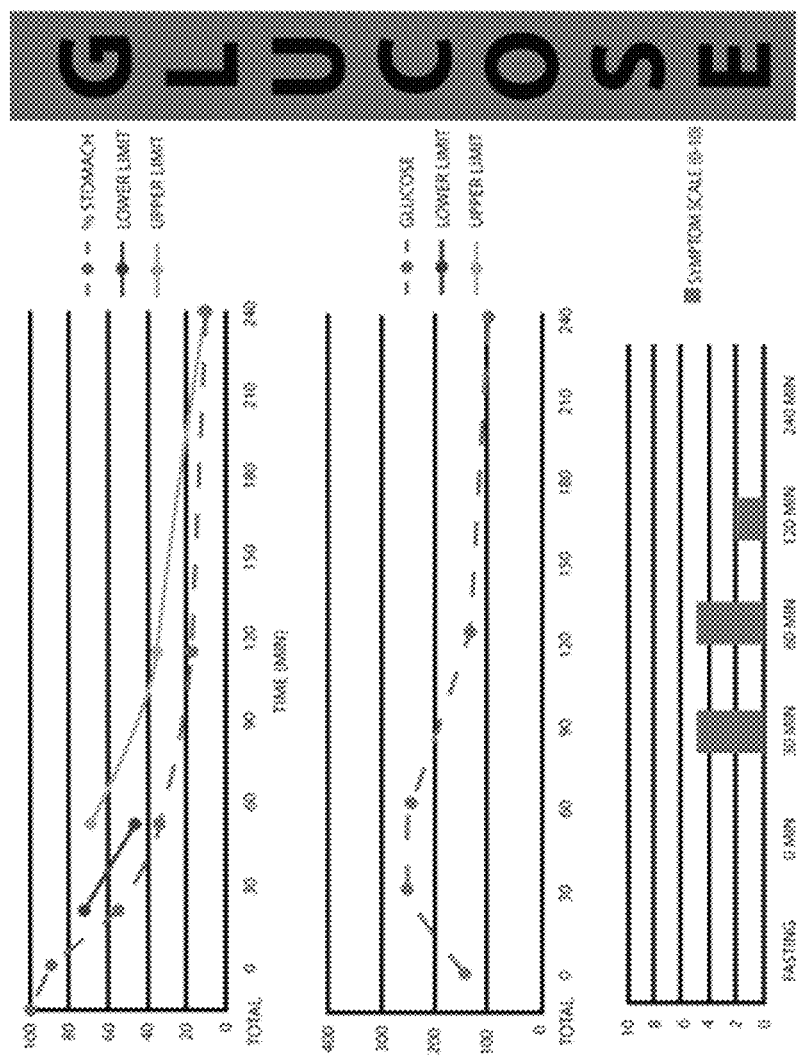
FIGS. 4D-4F are graphical representations of rapid carbohydrate emptying (FIG. 4D), elevated postprandial glycemic excursion (FIG. 4E) and a symptom scale (FIG. 4F) of a patient.

In contrast, FIGS. 4A-4F show an example of a patient with a normal solid gastric-emptying rate but an abnormally elevated glycemic excursion, which was further assessed with a liquid glucose gastric-emptying study. FIGS. 4A-4C are graphical representations of normal solid gastric emptying (FIG. 4A), elevated postprandial glycemic excursion (FIG. 4B) and a symptom scale (FIG. 4C) of a patient. FIGS. 4D-4F are graphical representations of rapid carbohydrate emptying (FIG. 4D), elevated postprandial glycemic excursion (FIG. 4E) and a symptom scale (FIG. 4F) of a patient. This patient has significantly elevated postprandial glycemic excursion (FIG. 4B) consistent with rapid carbohydrate emptying. So, this patient, 1 of the 9 who returned for dual assessments of GES techniques, demonstrated an abnormally rapid GES, which would have been undetected using standard protocols for GES. During both the solid and the liquid gastric-emptying studies, the patient had significant postprandial pain within the first hour after meal consumption (FIGS. 4C and 4F).

These data support the association of elevated solid meal glycemic excursions within the first hour with rapid emptying of the nonlabeled carbohydrate-containing components contained in the solid meal. An example of a patient with delayed solid emptying and an abnormally diminished glycemic excursion is shown in FIGS. 5A-5C. FIGS. 5A-5C are graphical representations of delayed solid gastric emptying (FIG. 5A), diminished postprandial glycemic excursion (FIG. 5B) and a symptom scale (FIG. 5C) of a diabetic patient. FIG. 5C shows a diabetic subject with delayed pain symptoms consistent with neuropathic gastroparesis. This pattern is most likely associated with delayed gastric emptying of the carbohydrate meal components as well as the protein meal component that would be expected with a vagal neuropathy.

Figures 6A, 6B, 6C:
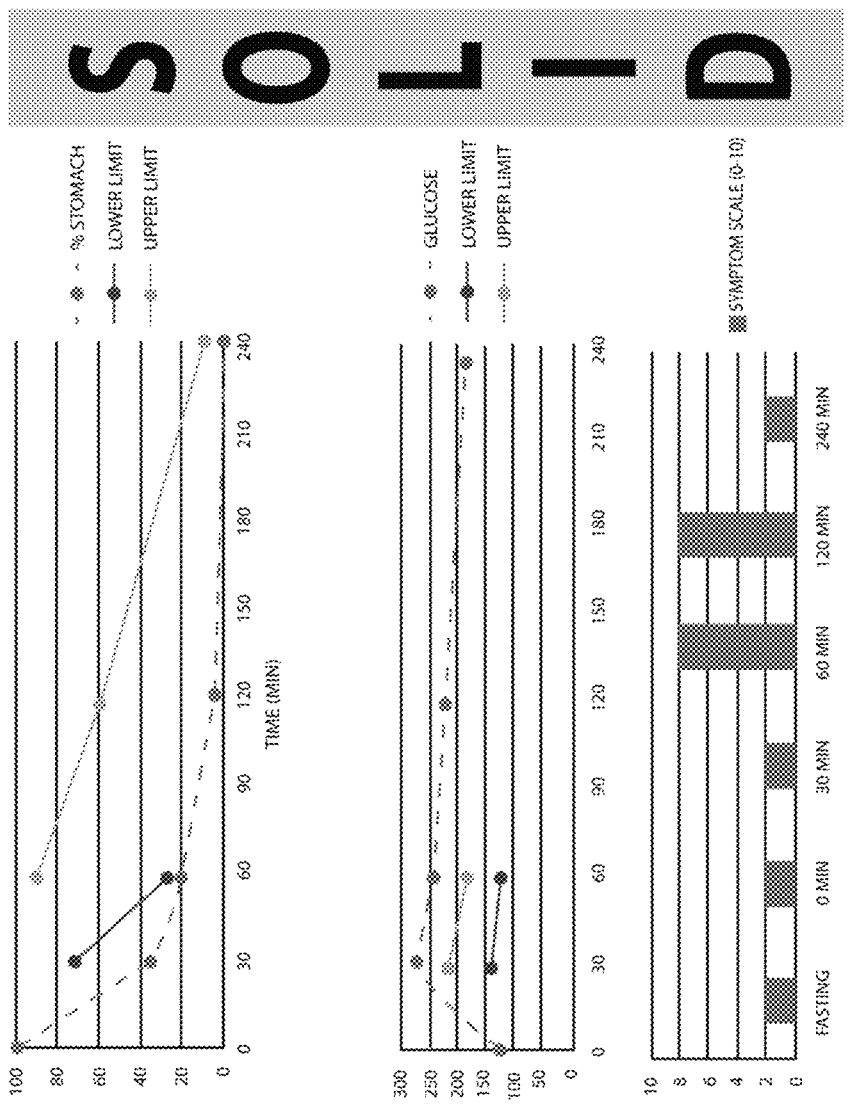
FIGS. 6A-6C are graphical representations of rapid solid gastric emptying (FIG. 6A), elevated postprandial glycemic excursion (FIG. 6B) and a symptom scale (FIG. 6C) of a diabetic patient.

Lastly, 25 of the 197 patients had rapid solid gastric emptying. FIGS. 6A-6C are graphical representations of rapid solid gastric emptying (FIG. 6A), elevated postprandial glycemic excursion (FIG. 6B) and a symptom scale (FIG. 6C) of a diabetic patient. FIGS. 6A-6C show a diabetic patient with rapid solid gastric emptying and an elevated glycemic excursion associated with early postprandial pain.

Only 2 of the 197 patients had abnormally rapid solid gastric emptying and an abnormally diminished glycemic excursion as shown in FIGS. 7A-7C. FIGS. 7A-7C are graphical representations of rapid initial solid gastric emptying (FIG. 7A), diminished postprandial glycemic excursion (FIG. 7B) and a symptom scale (FIG. 7C) of a patient. Two of the 197 patients in this study had this pattern of rapid gastric emptying and a significantly diminished glycemic excursion. This pattern is consistent with patients who have malabsorption of the carbohydrate portion of the standardized meal. Interestingly, both of these patients complained of significant bloating and diarrhea. Then, 9 patients with either normal or delayed gastric emptying, who were also having elevated postprandial glucose excursions during the first hour, were referred back for further assessment using liquid glucose GES to investigate whether an elevated glycemic excursion leads to otherwise undetected rapid rates of isolated carbohydrate gastric emptying.

Figure 9A:
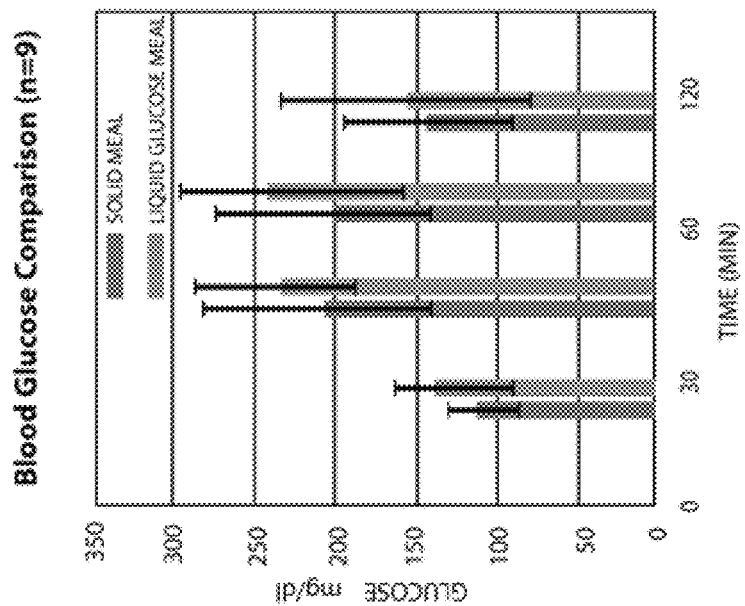
FIGS. 9A-9C are graphical representations of the blood glucose (FIG. 9A), average solid emptying (FIG. 9B), and average liquid glucose emptying (FIG. 9C) in 9 patients (7 diabetic and 2 nondiabetic).
Figure 9B:
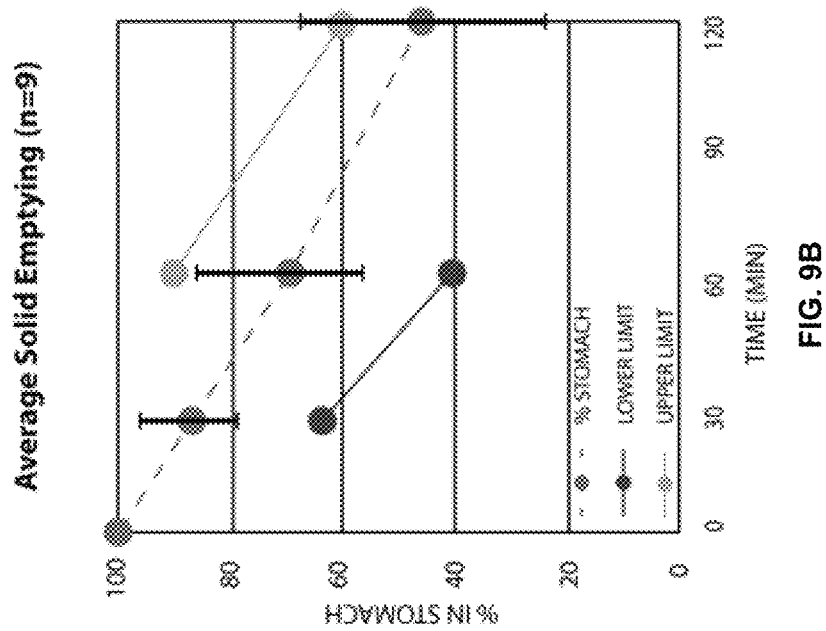
Figure 9C:
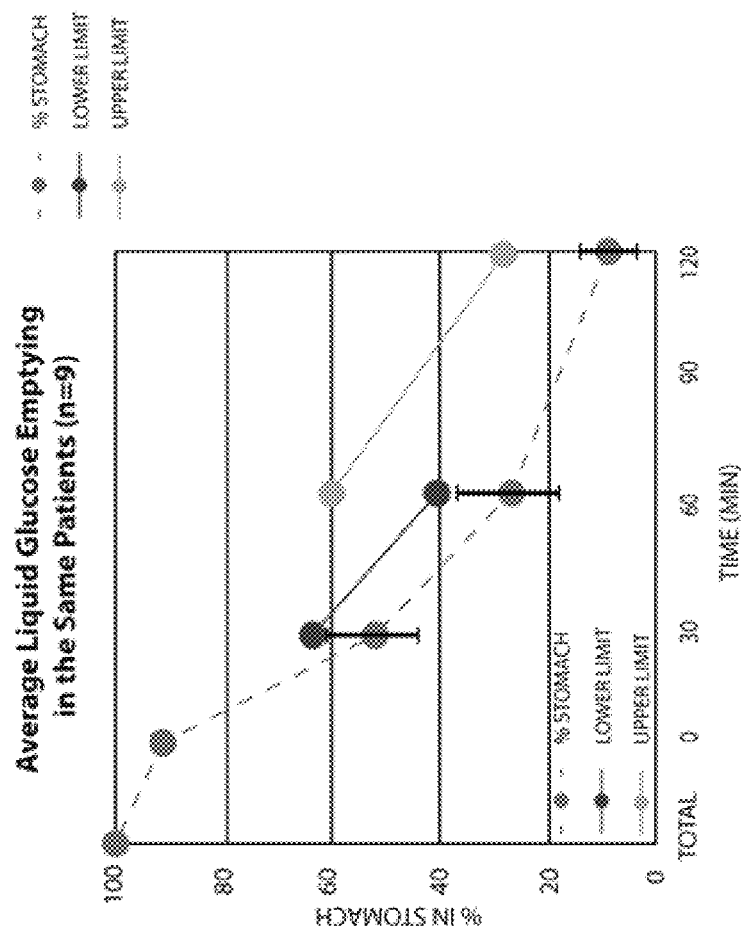

FIGS. 9A-9C are graphical representations of the blood glucose level (FIG. 9A), average solid emptying (FIG. 9B), and average liquid glucose emptying (FIG. 9C) in 9 patients (7 diabetic and 2 nondiabetic). Comparison of the average glycemic excursions between the 2 meals is shown in FIG. 9A. All of these 9 patients had abnormally elevated glucose excursions during the solid meal as well as during the liquid glucose meal. All 9 of these patients were found to have rapid liquid glucose carbohydrate gastric emptying with abnormally elevated postprandial blood glycemic excursions, which were not significantly different between the glucose and the solid meal, (P=0.3 at 30 minutes, P=0.19 at 1 hour, and P=0.73 at 2 hours) as shown in FIG. 9A. Average gastric emptying of the solid meal in the 9 patients was within normal limits as shown in FIG. 9B. Abnormally rapid average gastric emptying of the liquid glucose meal for these same 9 patients is shown in FIG. 9C. Note the exponential pattern of emptying of the liquid glucose meal, similar to the exponential pattern expected in gastric emptying of water, even though this liquid glucose meal has been previously reported to empty in a linear fashion in normal, nonsymptomatic subjects.

The association between gastric-emptying abnormalities and patient's gastrointestinal symptoms have not always correlated well. Based on the study disclosed here, at least one factor underlying the poor correlation between gastric symptoms and the rate of gastric emptying may be related to unrecognized abnormal gastric emptying of unlabeled meal components. A significant number of patients with normal or delayed gastric emptying of the solid egg white meal component appear to have rapid emptying of the carbohydrate meal components. Eighty-six of 172 patients with normal or delayed solid gastric emptying also had an abnormally elevated postprandial glycemic excursion. Surprisingly, 26 of the 54 patients with delayed solid emptying were also shown to have an abnormally elevated glycemic excursion consistent with these patients having rapid carbohydrate emptying during the first hour of the study, which was then followed by delayed emptying of the radiolabeled solid egg-white meal component. In this study, it was an unexpected result to find that more than 50% of all the patients had an abnormally elevated glycemic excursion with the standardized egg-white, bread, and jam meal. Although it is possible that some of these patients have severe insulin resistance as a cause of their elevated postprandial glycemic excursions, prior studies have shown that high glycemic excursions within the first hour are commonly associated with rapid gastric emptying of carbohydrate meal components. Rapid gastric emptying of carbohydrates has been previously reported to be common in diabetic patients, and this may explain the high percentage of patients with elevated glycemic excursions in this study because the majority of the patients had diabetes (Table 2). In this study, almost 30% of the nondiabetic subjects also had elevated glycemic excursions. These nondiabetic patients are likely at increased risk of developing diabetes as several studies have suggested that nondiabetic patients with rapid gastric emptying and elevated postprandial glycemic excursions are at increased risk of developing diabetes. These nondiabetic subjects may have metabolic syndrome as prior studies have shown that patients with markers of metabolic syndrome have more rapid gastric emptying. Different meal components could potentially empty at different rates, as fats, proteins, and carbohydrates are digested by different enzymes, and their rate of gastric emptying is controlled by different incretin hormones secreted from small intestine incretin cells. Carbohydrates are typically digested and triturated into liquid form more rapidly than proteins. The antropyloric contractions in conjunction with partial opening and closing of the pylorus result in a "sieving effect" in which small particles continuously flow from the stomach to the duodenum, whereas the larger particles are retropelled and retained in the stomach for further digestion. As previously discussed, it is also true that different meal macronutrients are under different hormonal controls. Based on the observations in this study, it appears that the majority of patients would benefit from having an isolated carbohydrate meal GES in addition to the standardized solid egg-white meal GES for a more comprehensive characterization of their gastric emptying.

Alternatively, it may be possible to develop a dual isotope-radiolabeled meal protocol enabling the carbohydrate and protein components of the meal to be tracked separately during the same meal. Dual-isotope gastric-emptying studies have already been described using $^{99m}$Tc—SC to label minced beef and $^{113m}$In-DTPA or $^{67}$Ga-EDTA to label 10% dextrose. Simultaneous blood glucose monitoring during the gastric emptying study appears to be a valuable addition to the standardized GES protocol, which is inexpensive and relatively easy to perform. Embodiments of methods of treatment of functional dyspepsia include the steps of classifying a subject as having a rapid carbohydrate gastric emptying based on a gastric-emptying scintigraphy assessment with labeled carbohydrates; and administering an amylin analogue or a CCK composition to the subject upon being classified as having rapid carbohydrate gastric emptying.

Monitoring postprandial glycemic excursion appears to provide a useful indicator for the emptying of the unlabeled carbohydrate component in the standardized meal. All 9 patients who returned for liquid glucose GES had abnormally elevated carbohydrate gastric emptying. As shown in this study, glucose monitoring during the standardized solid egg-white meal gastric-emptying study can screen patients for rapid gastric emptying of unlabeled carbohydrate meal components. Postprandial glucose levels can also clarify a neuropathic pattern of gastric emptying in which an abnormally diminished glycemic excursion is consistent with both the carbohydrate meal component and the radiolabeled egg white having delayed gastric emptying as would be expected for gastroparesis due to vagal nerve deterioration. The early postprandial symptoms noted in many of the patients with elevated glycemic excursions are similar to symptoms observed in patients with functional dyspepsia. In this study, patients with delayed solid gastric emptying were twice as likely to have elevated glycemic excursions in the first hour as to have diminished glycemic excursions. The monitoring of glucose during the standardized gastric emptying study can provide valuable information for assessing each patient and developing a patient management plan.

The amylin analogue, pramlintide significantly decreased the rate of gastric emptying. Pramlintide delays the rate of gastric emptying of a liquid half time of 30 minutes to a gastric emptying half time of 110 minutes. Pramlintide can be administered for the treatment of functional dyspepsia. Pramlintide is also ideal for non-diabetic patients in that it does not affect insulin and would not lower blood glucose levels to hypoglycemic levels. An infusion of CCK analogue delays gastric emptying from a half emptying time of 41 minutes to a half time of 91 minutes. Therefore, CCK analogues are another class of agents for the treatment of functional dyspepsia.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treatment of functional dyspepsia in a subject, the method including the steps of:
classifying the subject as having normal or delayed gastric emptying based on a standard gastric-emptying scintigraphy assessment using a standardized solid meal;
classifying the subject as having elevated glycemic excursion due to rapid carbohydrate gastric emptying based on one or more measurements of blood glucose levels of the subject during the standard gastric-emptying scintigraphy assessment; and
administering an amylin analogue to the subject upon being classified as having normal or delayed solid gastric emptying and elevated glycemic excursion.

2. The method of claim 1, wherein the amylin analogue is pramlintide.

3. The method of claim 2, wherein the pramlintide is administered via a parenteral route.

4. The method of claim 1, where the subject is a non-diabetic individual.

5. A method of treatment of functional dyspepsia in a subject, the method including the steps of:
classifying the subject as having normal or delayed gastric emptying based on a standard gastric-emptying scintigraphy assessment using a standardized solid meal, wherein the subject has emptied less than 90% of a standardized solid meal at 4 hours, less than 10% of the standardized solid meal at 1-2 hours, 30% or less of the standardized solid meal at 30 minutes, and/or 70% or less of the standardized solid mean at 1 hour;
classifying the subject as having elevated glycemic excursion due to rapid carbohydrate gastric emptying based on one or more measurements of blood glucose levels of the subject during the standard gastric-emptying scintigraphy assessment; and
administering an amylin analogue to the subject upon being classified as having normal or delayed solid gastric emptying and elevated glycemic excursion.

6. A method of treatment of functional dyspepsia in a subject, the method including the steps of:
classifying the subject as having normal or delayed gastric emptying based on a standard gastric-emptying scintigraphy assessment using a standardized solid meal;
classifying the subject as having elevated glycemic excursion due to rapid carbohydrate gastric emptying based on one or more measurements of blood glucose levels of the subject during the standard gastric-emptying scintigraphy assessment, wherein the glycemic excursion above baseline was greater than 75 mg/dL at 30 minutes or greater than 85 mg/dL at 1 hour; and
administering an amylin analogue to the subject upon being classified as having normal or delayed solid gastric emptying and elevated glycemic excursion.

* * * * *